United States Patent [19]

Marciel

[11] Patent Number: Plant 6,582

[45] Date of Patent: Feb. 7, 1989

[54] ROSE PLANT NAMED DE VORAN

[75] Inventor: Stanley G. Marciel, Pleasanton, Calif.

[73] Assignee: DeVor Nurseries, Inc., Pleasanton, Calif.

[21] Appl. No.: 70,729

[22] Filed: Jul. 7, 1987

[51] Int. Cl.[4] ..... A01H 5/00

[52] U.S. Cl. ..... Plt./16

[58] Field of Search ..... Plt./16

*Primary Examiner*—James R. Feyrer

*Attorney, Agent, or Firm*—Charles W. Rummler

[57] ABSTRACT

A new orange-yellow hybrid tea rose distinguished by its profuse and continuous year around production of very large flowers borne on vigorous, sturdy and upright stems reaching a height of about 142 cm; and by its vigorous, free branching growth habit and the long lasting character of its flowers both on the plant and as cut flowers.

1 Drawing Sheet

BACKGROUND OF THE INVENTION

This new rose plant resulted from a selected seedling produced by me at Pleasanton, Calif., by my crossing of the variety 'Yellow Perfection' (U.S. Plant Pat. No. 1,083) with the vareity 'Cocktail' (unpatented) as the pollen parent with the object of obtaining a new variety of orange-yellow hybrid tea rose with large flowers long lasting after being cut. Asexual propagation of this selected seedling was done by me and under my direction by budding and this manner of reproduction was carried on through several successive generations, which demonstrated clearly that the novel and distinctive features of this new plant would hold true from generation to generation and appeared to be firmly fixed.

DESCRIPTION OF THE DRAWING

My new rose plant is illustrated by the accompanying photographic drawing, the upper view of which is a face view in full color of a newly opened flower and the lower view shows the flower parts, including two forms of the leaf, a fully opened bloom, a bud stem showing a bud about to open and various parts, including a piece of wood showing the nature of the thorns, the color rendition being as nearly true to those specified herein as is reasonaby possible to obtain by conventional photographic procedures.

DESCRIPTION OF THE NEW VARIETY

The following is a detailed description of my new rose plant based upon observation of plants grown in greenhouse at Pleasanton, Calif., the color designations being according to the R.H.S. Colour Chart published by The Royal Horticultural Society of London, England.

THE PLANT

Origin: Seedling.

Parentage:

*Seed parent.*—'Yellow Perfection' (U.S. Plant Pat. No. 1,083).

*Pollen parent.*—'Cocktail' (unpatented).

Classification:

*Botanic.*—Hybrid Tea.

*Commercial.*—Greenhouse Rose.

Form: Upright bush.

Growth rate: Very vigorous.

Height: About 142 cm.

Cane length: About 110 cm. to the peduncle of the flower.

*Color.*—Green, 138A.

Branching character: Free branching.

Growth: Vigorous, upright, with strong cones and stems.

Foliage:

*Quantity.*—Abundant.

*Number of leaves.*—About 8 to 10 on cut flower stem.

*Leaf size.*—About 80 mm. long and about 51 mm. wide.

*Shape.*—Oval.

*Leaflets.*—Number: 3 to 7. Size: About 32 mm. long and about 20 mm. wide. Shape: Oval with denticulate margins.

*Texture.*—Leathery.

*Aspect.*—Semi-glossy.

*Color.*—Upper side — Green, 137A. Under side — Greyed Green, 191A, mottled with Red Group 55A.

*Stipules.*—Thread-like with very fine hairs on edge.

*Petiolule.*—Length: About 2 mm.

*Rachis.*—About 61 mm. long.

*Petioles.*—About 6 mm. long.

*Ribs and veins.*—Fairly prominent on bottom but slightly depressed on upper surface.

Thorns: The plant has thorns but they are sparse.

*Color.*—Greyed Orange. 175A.

*Size.*—About 6 mm. long.

THE BUD

Form: Long, pointed, urn shaped.

Size: Medium.

*Diameter.*—About 30 mm.

*Length.*—About 40 mm.

Opening rate: Slow.

Color of petals:

*When petals first divide.*—Yellow, 8B, tinged with Red, 45C.

*When sepals begin to unfurl.*—Orange-Red, 30B, and Yellow, 13B.

Sepals:

*Number.*—Five.

*Shape.*—Long lanceolate and curled back as petals begin to unfurl.

*Color.*—Inside — Yellow-Green, 147D. Outside — Green, 139C.

Calyx:

*Shape.*—Funnel-shaped.

*Size.*—Large.

*Aspect.*—Smooth.

*Splitting.*—The calyx does not split.

Peduncle of flower stem:

*Length.*—About 80 mm.

*Character.*—Erect and rigid.

*Color.*—Yellow-Green, 144B.

THE FLOWER

Blooming habit: Continuous and profusely the year around. The plant blooms freely in Fall under glass-house conditions.

Size: Very large.

*Diameter.*—About 100 mm.

*Depth.*—About 40 mm.

Borne: Singly.

Form: High centered when bloom first opens, becoming nicely imbricated when bloom matures.

Petalage:

*Number.*—About 24 to 26.

*Arrangement.*—Imbricated.

*Form.*—Obovate with smooth margins and mucronate apex.

*Texture.*—Semi-leathery.

*Aspect.*—Satiny

*Color.*—Outer petals: Upper side: Body — Orange-Red, 30B. Base — Yellow, 13B. Color measurement — 30B, about 20 mm.; 13B, about 20 mm. Reverse side: Body — Yellow, 8A, with margin of Red, 40B. Color measurement — 40B, about 1 mm.; 8A, about 39 mm. Inside petals: Upper side: Body — Orange-Red, 30B. Base — Yellow, 13B. Color measurement — 30B, about 15 mm.; 13B, about 15 mm. Reverse side: Body — Red, 40B. Base — Yellow, 8A. Color measurement — 40B, about 1 mm.; 8A, about 29 mm.

Petaloids:

*Number.*—Two.

*Size.*—About 22 mm. long.

*Color.*—Red, 30B, with Yellow, 13B.

Peduncle or flower stem:

*Length.*—About 80 mm.

*Color.*—Yellow-Green, 144B.

*Character.*—Sturdy and upright.

Persistence: The petals hang on and dry.

Fragrance: Slightly fragrant.

Disease resistance: Moderately resistant to mildew, rust and black spot as observed at Pleasanton, Calif.

Lasting quality:

*On plant.*—About 12 to 14 days.

*As cut flower.*—About 10 to 12 days.

REPRODUCTIVE ORGANS

Stamens:

*Number.*—About 163 in slightly introrse arrangement.

*Anthers.*—Size: About 2 mm. Color: Yellow-Orange, 16A.

*Filaments.*—Length: About 8 mm. Color: Yellow, 9B.

*Pollen.*—Color: Yellow-Orange, 16A.

Pistils:

*Number.*—About 140.

*Styles.*—Length: About 8 mm. Color: Red, 39B.

*Stigmas.*—Color: Yellow-Orange, 22C.

Character of ovaries: Large, funnel shaped and slightly rounded with silver threads covering the entire ovary.

I claim:

1. The new and distinct variety of rose plant and parts thereof, substantially as herein shown and described, characterized by the very large size of its orange-yellow blooms, which are produced continuously and profusely with sturdy, upright peduncles on a very tall plant of free branching character with vigorous, upright and strong canes, moderately abundant foliage, and very vigorous growth rate.

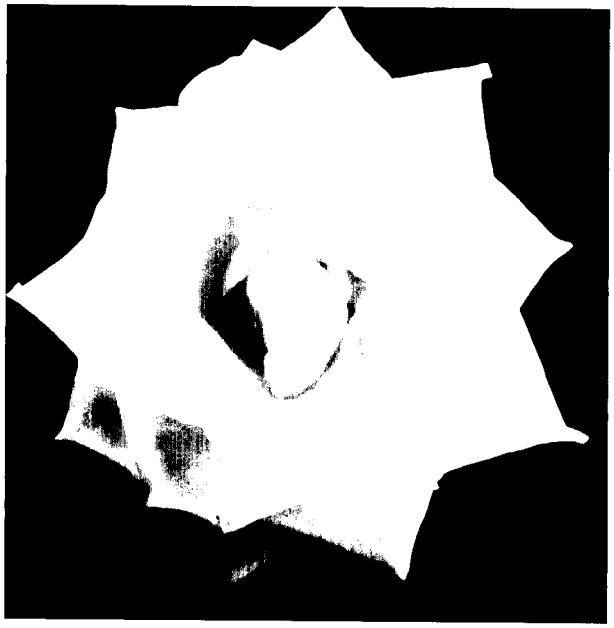
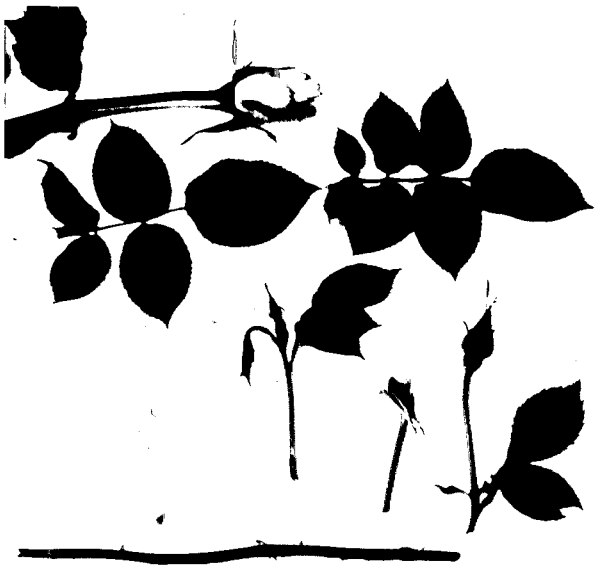

* * * * *